US010183958B2

(12) United States Patent
Gohndrone

(10) Patent No.: US 10,183,958 B2
(45) Date of Patent: *Jan. 22, 2019

(54) METHOD OF PRODUCING ORGANOHALOSILANES

(71) Applicant: Dow Silicones Corporation, Midland, MI (US)

(72) Inventor: John Michael Gohndrone, Midland, MI (US)

(73) Assignee: Dow Silicones Corporation, Midland, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/527,537

(22) PCT Filed: Feb. 3, 2016

(86) PCT No.: PCT/US2016/016343
§ 371 (c)(1),
(2) Date: May 17, 2017

(87) PCT Pub. No.: WO2016/126804
PCT Pub. Date: Aug. 11, 2016

(65) Prior Publication Data
US 2018/0105542 A1    Apr. 19, 2018

Related U.S. Application Data

(60) Provisional application No. 62/112,863, filed on Feb. 6, 2015.

(51) Int. Cl.
C07F 7/14      (2006.01)
B01J 21/04     (2006.01)
B01J 21/06     (2006.01)
B01J 37/24     (2006.01)
B01J 37/08     (2006.01)
C07F 7/12      (2006.01)
B01J 21/12     (2006.01)

(52) U.S. Cl.
CPC ............ C07F 7/125 (2013.01); B01J 21/04 (2013.01); B01J 21/066 (2013.01); B01J 21/12 (2013.01); C07F 7/126 (2013.01); B01J 2523/305 (2013.01); B01J 2523/31 (2013.01); B01J 2523/41 (2013.01); B01J 2523/48 (2013.01)

(58) Field of Classification Search
None
See application file for complete search history.

(56) References Cited

U.S. PATENT DOCUMENTS

| 2,775,606 | A | 12/1956 | Wagner et al. |
| 4,543,347 | A | 9/1985 | Heyward et al. |
| 4,889,838 | A | 12/1989 | Lewis et al. |
| 5,136,070 | A | 8/1992 | Bank |
| 5,220,069 | A | 6/1993 | King et al. |
| 6,087,523 | A | 7/2000 | Bank et al. |
| 6,177,585 | B1 | 1/2001 | Chen et al. |
| 6,271,407 | B1 | 8/2001 | Colin et al. |
| 6,632,956 | B2 | 10/2003 | Tsukuno et al. |
| 6,686,492 | B2 | 2/2004 | Nguyen |
| 6,747,168 | B2 | 6/2004 | Chaturvedi et al. |
| 8,367,856 | B2 | 2/2013 | Mautner et al. |
| 8,492,592 | B2 | 7/2013 | King et al. |
| 8,962,877 | B2 | 2/2015 | Kohane et al. |
| 9,296,765 | B2 | 3/2016 | Coppernoll et al. |
| 9,908,903 | B2 * | 3/2018 | Gohndrone ............... C07F 7/14 |
| 2011/0132744 | A1 | 6/2011 | Auner et al. |
| 2013/0072710 | A1 | 3/2013 | Brazdil et al. |

FOREIGN PATENT DOCUMENTS

| JP | 31-009980 | 3/1954 |
| JP | 35-003018 | 12/1995 |

OTHER PUBLICATIONS

A.J. Barry, J.W. Gilkey, and D.E. Hook, "Preparation of Arylhalosilanes", Advances in Chemistry vol. 51(2), Feb. 1959.
A. Wright, The Role of Boron Trichloride in the Synthesis of Phenyltrichlorosilane from Benzene and Trichlorosilane, J.Org. Chem. vol. 145, pp. 307-314, (1978).
Office Action from corresponding Japanese 2017-541057 application, dated May 7, 2018.

* cited by examiner

Primary Examiner — Clinton A Brooks
(74) Attorney, Agent, or Firm — Catherine U. Brown

(57) ABSTRACT

A method for producing an organohalosilanes comprising reacting an organic compound comprising a halogen-substituted or unsubstituted alkane, a halogen-substituted or unsubstituted alkene, or an aromatic compound and at least one hydridohalosilane of formula $R_nSiH_mX_{4-m-n}$, wherein each R is independently $C_1$-$C_{14}$ hydrocarbyl or $C_1$-$C_{14}$ halogen-substituted hydrocarbyl, X is fluoro, chloro, bromo, or iodo, n is 0, 1, or 2, m is 1, 2 or 3, and m+n=1, 2 or 3, in the presence of a heterogeneous catalyst comprising an oxide of one or more of the elements Sc, Y, Ti, Zr, Hf, B, Al, Ga, In, C, Si, Ge, Sn, or Pb, at a temperature greater than 100° C., and at a pressure of at least 690 kPa, to produce a crude reaction product comprising the organohalosilane.

16 Claims, No Drawings

METHOD OF PRODUCING ORGANOHALOSILANES

This application is a U.S. national stage filing under 35 U.S.C. § 371 of PCT Application No. PCT/US16/016343 filed on 3 Feb. 2016, which claims the benefit of U.S. Provisional Patent Application No. 62/112,863 filed 6 Feb. 2015 under 35 U.S.C. § 119 (e). PCT Application No. PCT/US16/016343 and U.S. Provisional Patent Application No. 62/112,863 are hereby incorporated by reference.

The present invention relates to methods of producing organohalosilanes and, more particularly, to methods comprising reacting an organic compound comprising a halogen-substituted or unsubstituted alkane, halogen-substituted or unsubstituted alkene or aromatic compound with a hydridohalosilane in the presence of a heterogeneous catalyst comprising an oxide of one or more of the elements Sc, Y, Ti, Zr, Hf, B, Al, Ga, In, C, Si, Ge, Sn, or Pb.

Processes for making aromatic organohalosilanes through reactions with hydridohalosilanes are known. In one such process, hydrocarbons and alkyl-substituted benzenoids were reacted with trichlorosilane in the presence of a soluble boron halide catalyst at a temperature above 230° C. and under pressure to produce, for example, phenyltrichlorosilane. Other variations of this process have also been described using similar reaction conditions. For example, polyhalomonohydridosilanes, such as those containing one hydrogen atom and two halogen atoms bonded to the silicon atom and the remaining valence on the silicon being taken up by a monovalent hydrocarbon radical, have been reacted with benzenoid hydrocarbons using a boron halide catalyst. In another example, silicon-borate catalysts, which are soluble in the reaction medium, have been used in the reaction between trichlorosilane and naphthalene or benzenoid hydrocarbons free of any aliphatic unsaturation to produce aromatic chlorosilanes. In yet another example, mixtures of dichlorosilane and trichlorosilane have been reacted with benzene in the presence of a soluble Lewis acid metal halide and a metal hydride complex to favor production of phenyldichlorosilane over phenyltrichlorosilane or diphenyldichlorosilane. In still another variation, aromatic halohydrocarbons have been reacted with methyldichlorosilane in the presence of soluble boron trichloride or soluble aluminum chloride to produce an organodichlorosilyl derivative of the aromatic halohydrocarbon without displacement of the halogen from the aromatic ring structure.

Organohalosilanes have also been made by reacting an olefin with a hydridohalosilane in the presence of a supported heterogeneous transition metal catalyst. For example, hydridohalosilanes have been reacted with olefins in the presence of supported platinum catalysts.

The inventors have found existing processes for producing organohalosilanes by the reaction of an organic compound, such as an aromatic compound, with a hydridohalosilane in the presence of a catalyst are deficient in some respects. For example, catalysts used in the processes described above with aromatic organic compounds are homogeneous catalysts, which are difficult to remove from the crude product. The presence of catalyst in the crude product can cause issues in the recovery of the product. For example, the product is typically recovered through distillation, but typical homogeneous or soluble catalysts can catalyze rearrangement reactions in the distillation column reducing yields and increasing unwanted byproducts. To avoid these rearrangement reactions, the catalyst can be deactivated before distillation through the addition of a catalyst poison; however, addition of a poison increases the cost and complexity of the process, introduces an additional, unwanted material, and renders the catalyst unusable and unrecyclable.

Hydrosilation reactions involving reaction of a hydridohalosilane in the presence of a transition metal catalyst are limited to olefins and are not effective across aryl or alkyl C—H bonds.

Finally, in addition to the deficiencies of current processes described above related to the separation of catalyst form the reaction products and catalyst effectiveness across aryl and alkyl C—H bonds, there also exist needs related to process economics and safety such as improving reaction yields, catalyst reuse, reducing reaction pressures, and reducing reaction temperatures.

BRIEF SUMMARY OF THE INVENTION

The invention is directed to a method for producing an organohalosilane comprising reacting an organic compound comprising a halogen-substituted or unsubstituted alkane, a halogen-substituted or unsubstituted alkene, or aromatic compound and at least one hydridohalosilane of formula $R_nSiH_mX_{4-m-n}$, wherein each R is independently $C_1$-$C_{14}$ hydrocarbyl or $C_1$-$C_{14}$ halogen-substituted hydrocarbyl, X is fluoro, chloro, bromo, or iodo, n is 0, 1, or 2, m is 1, 2 or 3, and m+n=1, 2 or 3, in the presence of a heterogeneous catalyst comprising an oxide of one or more of the elements Sc, Y, Ti, Zr, Hf, B, Al, Ga, In, C, Si, Ge, Sn, or Pb, at a temperature greater than 100° C., and at a pressure of at least 690 kPa, to produce a crude reaction product comprising the organohalosilane.

Depending upon the embodiment, the method of the invention may produce organohalosilanes at lower pressure and temperature, with better yields, with fewer byproducts, and more economically than known processes. In addition, the method employs a heterogeneous catalyst that can be easily removed from the crude reaction product.

The organohalosilane products of the present method are used as precursors to make many different commercial products including arylsiloxanes which also have many commercial uses.

DETAILED DESCRIPTION OF THE INVENTION

The Brief Summary and Abstract are incorporated here by reference. The invention embodiments, uses and advantages summarized above are further described below.

Aspects of the invention are described herein using various common conventions. For example, all states of matter are determined at 25° C. and 101.3 kPa unless indicated otherwise. All % are by weight unless otherwise noted or indicated. All % values are, unless otherwise noted, based on total amount of all ingredients used to synthesize or make the composition, which adds up to 100%. Any Markush group comprising a genus and subgenus therein includes the subgenus in the genus, e.g., in "R is hydrocarbyl or alkenyl," R may be alkenyl, alternatively R may be hydrocarbyl, which includes, among other subgenuses, alkenyl.

Aspects of the invention are described herein using various patent terms. For example, "alternatively" indicates a different and distinct embodiment. "Comparative" as used in comparative example, comparative process or comparative method means a non-invention experiment and should not be interpreted as prior art. "Comprises" and its variants (comprising, comprised of) are open ended. "Consists of" and its variants (consisting of) are closed ended. "Contacting" means bringing into physical contact. "May" confers a choice, not an imperative. "Optionally" means is absent, alternatively is present.

The present invention is directed to a method for producing an organohalosilane, the method comprising: reacting an organic compound comprising a halogen-substituted or unsubstituted alkane, a halogen-substituted or unsubstituted alkene, or an aromatic compound and at least one hydridohalosilane of formula $R_nSiH_mX_{4-m-n}$, wherein each R is independently $C_1$-$C_{14}$ hydrocarbyl or $C_1$-$C_{14}$ halogen-substituted hydrocarbyl, X is fluoro, chloro, bromo, or iodo, n is 0, 1, or 2, m is 1, 2 or 3, and m+n=1, 2 or 3, in the presence of a heterogeneous catalyst comprising an oxide of one or more of the elements Sc, Y, Ti, Zr, Hf, B, Al, Ga, In, C, Si, Ge, Sn, or Pb, at a temperature greater than 100° C., and at a pressure of at least 690 kPa, to produce a crude reaction product comprising the organohalosilane.

The organic compound comprises a halogen-substituted or unsubstituted alkane, a halogen-substituted or unsubstituted alkene, and/or a halogen-substituted or unsubstituted aromatic compound. The organic compound has from 1 to 14 carbon atoms; alternative from 4 to 10 carbon atoms; alternatively from 4 to 8 carbon atoms; alternatively from 6 to 8 carbon atoms. Organic compounds can have a branched, unbranched, cyclic or polycyclic, such as fused, bridged, or spiro structure.

Examples of unsubstituted alkanes include, but are not limited to, non-cyclic, linear or branched alkanes such as methane, ethane, propane, n-butane, isobutane, n-pentane, isopentane, neopentane, 2-methylpentane, 3-methylpentane, 2,3-dimethylbutane, n-hexane, neohexane, heptane, octane, nonane, decane, undecane, dodecane, tridecane, tetradecane; cyclic alkanes, such as cyclopropane, cyclobutane, cyclopentane, cyclohexane, methylcyclohexane, cycloheptane, bicyclo[2.2.1]heptane, methylcycloheptane, cyclooctane, cyclononane, bicyclo[3.3.1]nonane, cyclodecane, bicyclo[4.3.1]decane, cycloundecane, and cyclododecane. Examples of halogen-substituted alkanes include, but are not limited to, the alkanes exemplified above with a fluorine, chlorine, bromine, or iodine atom, alternatively a chlorine atom, substituted for one of the hydrogen atoms of the alkane.

Examples of unsubstituted alkenes include, but are not limited to, non-cyclic, linear or branched alkenes such as the following alkenes and their isomers: ethene, propene, butene, pentene, 2-methylpentene, 3-methylpentene, 2,3-dimethylbutene, n-hexene, neohexene, heptene, octene, nonene, decene, undecene, dodecene, tridecene, tetradecene; cyclic alkenes, such as cyclopropene, cyclobutene, cyclopentene, cyclohexene, methylcyclohexene, cycloheptene, bicyclo[2.2.1]heptene, methylcycloheptene, cyclooctene, cyclononene, bicyclo[3.3.1]nonene, cyclodecene, bicyclo[4.3.1]decene, cycloundecene, cyclododecene. Examples of halogen-substituted alkenes include, but are not limited to, the alkenes exemplified above with a fluorine, chlorine, bromine, or iodine atom, alternatively a chlorine atom, substituted for one of the hydrogen atoms of the alkene. As used herein, "isomer" means a molecule having the same molecular formula, but having a different arrangement of atoms in space. For example, butane and its isomers would include 1-butene, cis-but-2-ene, trans-but-2-ene, and 2-methylpropene.

Examples of unsubstituted aromatic compounds include, but are not limited to, benzene, toluene, 1,3-dimethylbenzene, 1,4-dimethylbenzene, 1-phenylethene, 1-phenyl-1-propene, naphthalene, xylene, and 1,1-diphenylethene. Examples of halogen-substituted aromatic compounds include, but are not limited to, the aromatic compounds exemplified above with a fluorine, chlorine, bromine, or iodine atom, alternatively a chlorine atom, substituted for one of the hydrogen atoms of the aromatic compound, such as chlorobenzene or dichlorobenzene.

The hydridohalosilane is according to the formula $R_nSiH_mX_{4-m-n}$, where R is $C_1$-$C_{14}$ hydrocarbyl or $C_1$-$C_{14}$ halogen-substituted hydrocarbyl, X is fluoro, chloro, bromo, or iodo, alternatively X is chloro, n is 0, 1, or 2, alternatively n is 0 or 1, m is 1, 2 or 3, alternatively m is 1 or 2, alternatively m is 1, and m+n=1, 2 or 3, alternatively m+n is 1 or 2, alternatively m+n is 2. The hydrocarbyl groups represented by R typically have from 1 to 14 carbon atoms, alternatively from 1 to 10 carbon atoms, alternatively from 1 to 4 carbon atoms, alternatively 1 or 2 carbon atoms; alternatively 1 carbon atom. Acyclic hydrocarbyl groups containing at least 3 carbon atoms can have a branched or unbranched structure. Examples of $C_1$-$C_{14}$ hydrocarbyl groups represented by R include, but are not limited to, alkyl, such as methyl, ethyl, propyl, 1-methylethyl, butyl, 1-methylpropyl, 2-methylpropyl, 2-methylpropyl, 1,1-dimethylethyl, pentyl, 1-methylbutyl, 1-ethylpropyl, 2-methylbutyl, 3-methylbutyl, 1,2,-dimethylpropyl, 2,2-dimethylpropyl, hexyl, heptyl, octyl, nonyl, decyl, undecyl, dodecyl, tridecyl, and tetradecyl; cycloalkyl, such as cyclopentyl, cyclohexyl, and methylcyclohexyl; aryl, such as phenyl and naphthyl; alkaryl, such as tolyl and xylyl; aralkyl such as benzyl and phenylethyl; alkenyl, such as vinyl, allyl, propenyl, butenyl, hexenyl; alkynyl, such as ethynyl and propynyl.

Examples of the hydridohalosilanes according to the invention include, but are not limited to, monochlorosilane, dichlorosilane, trichlorosilane, methylchlorosilane, methyldichlorosilane, dimethylchlorosilane, ethylchlorosilane, ethyldichlorosilane, diethyichlorosilane, propylchlorosilane, propyldichlorosilane, dipropylchlorosilane, butylchlorosilane, butyldichlorosilane, dibutylchlorosilane, pentylchlorosilane, pentyldichlorosilane, dipentylchlorosilane, hexylchlorosilane, hexyldichlorosilane, dihexylchlorosilane, octylchlorosilane, octyldichlorosilane, dioctylchlorosilane, decylchlorosilane, decyldichlorosilane, didecylchlorosilane, tetradecylchlorosilane, tetradecyldichlorosilane, ditetradecylchlorosilane, phenylchlorosilane, phenyldichlorosilane, diphenylchlorosilane, vinylchlorosilane, vinyldichlorosilane, divinylchlorosilane, allylchlorosilane, allyldichlorosilane, diallylchlorosilane, benzylchlorosilane, benzyldichlorosilane, dibenzylchlorosilane, ethynylchlorosilane, ethynyldichlorosilane, diethynylchlorosilane, propynylchlorosilane, propynyldichlorosilane, dipropynylchlorosilane. In one embodiment, the hydrohalosilane is methyldichlorosilane, phenyldichlorosilane, dimethylchlorosilane, or diphenylchlorosilane. Methods of making the hydridohalosilanes of the invention are known in the art.

As used herein in reference to the catalyst, "heterogeneous" means that the catalyst is in its own phase in relation to the reactants and products, such as, but not limited to, a solid phase catalyst with a combination of gas, liquid, and supercritical phases for the reactants and/or products; "soluble" means that the catalyst and the reactants form one phase; and "oxide" means a compound having at least one oxygen and at least one other element in its chemical formula.

The heterogeneous catalyst comprises an oxide of one or more of the elements Sc, Y, Ti, Zr, Hf, B, Al, Ga, In, C, Si, Ge, Sn, or Pb, alternatively an oxide of one or more of Sc, Y, Ti, Zr, B, Al, Si, or Ge, alternatively an oxide of two or more of Sc, Y, Ti, Zr, Hf, B, Al, Ga, In, C, Si, Ge, Sn, or Pb, alternatively an oxide of two or more of Sc, Y, Ti, Zr, B, Al, Si, or Ge, alternatively alumina, zirconium dioxide, an oxide comprising Al and one of the elements B, Zr, Ti, or Si, or an oxide comprising Zr and one of the elements B, Ti, or Si, alternatively an oxide comprising Zr and B, Al and B, or Al and Si, alternatively γ-alumina or zirconium dioxide, alternatively an oxide comprising Al and B or an oxide comprising Zr and B, alternatively γ-alumina, alternatively an oxide of formula $Al_9B_2O_{15}$ or $Al_4B_2O_9$. It will be apparent to one skilled in the art that all of the oxides of the invention contain oxygen, and the oxygen atoms are present in the oxide in sufficient quantity to satisfy the valence requirements of the other atoms.

In one embodiment, the heterogeneous catalyst is an oxide of formula $M^1_aM^2_bM^3_cM^4_dO_x$, where $M^1$, $M^2$, $M^3$ and $M^4$ are each independently Sc, Y, Ti, Zr, Hf, B, Al, Ga, In, C, Si, Ge, Sn, or Pb, a, b, c, and d are each independently from 0 to 1, and a+b+c+d>0, and x>0 to 1, alternatively $M^1$, $M^2$ and $M^3$ are each independently Sc, Y, Ti, Zr, B, Al, Si, or Ge, a is from 0 to 1, b is from 0 to 1, c is from 0 to 1, d is 0, and a+b+c>0, alternatively $M^1$ is Ti, Zr, B, or Al, $M^2$ is Ti, Zr, B, or Al, $M^3$ is Sc or Y, $M^4$ is Si or Ge, a is from 0 to 1, b is from 0 to 1.00, c is from 0 to 0.10, d is from 0 to 0.50, a+b+c+d>0, and if a=0 then b>0 and when b=0 then a>0, alternatively $M^1$ is Al, $M^2$ is Zr, and $M^3$ is B, Ti, or Si, a is 0 or from 0 to 1, b is 0 or from 0 to 1, c is from 0 to 0.5 or from 0 to 0.3, d is 0, a+b+c>0, and if a=0 then b>0 and if b=0 then a>0, alternatively $M^1$ is Zr or Al, a is >0 to 1, and b, c, and d=0, and in all cases x is the number of oxygen atoms in the oxide and is sufficient in number to satisfy the valence of the other atoms in the oxide, alternatively x is from >0 to 1. The letters a, b, c, d, and x represent the gram-atom ratio of the elements present in the oxide. In all cases, $M^1$, $M^2$, $M^3$, and $M^4$ are all different elements when present in formula $M^1_aM^2_bM^3_cM^4_dO_x$.

Examples of the heterogeneous catalyst include, but are not limited to, alumina in any form, such as eta-alumina, nanosheets, α-alumina, and γ-alumina; zirconium dioxide, $ZrO_2$, in any form such as monoclinic, tetragonal, or cubic; composite oxides comprising the elements of Al and at least one of Ti, Zr, or B, including, but not limited to, oxides having the formula $Al_9B_2O_{15}$ and $Al_4B_2O_9$; and composite oxides of the element Zr and at least one or Ti, Al, or B. Alumina and zirconium dioxide are known in the art and available commercially in their different forms. For example, γ-alumina may be purchased from Clariant International, Ltd., of Munich, Germany.

The composition of the heterogeneous catalyst may be determined using methods known in the art. For example, one or more of elemental analysis, X-ray crystallography, electron microscopy, mass spectroscopy, and electrochemical methods known in the art may be used.

The heterogeneous catalyst may also comprise a binder or carrier. For example, the heterogeneous catalyst may comprise a graphite or aluminum stearate binder. Graphite and aluminum stearate are available commercially. Binders are typically used to control the shape of the heterogeneous catalyst.

In one embodiment, the heterogeneous catalyst comprises less than 25% (w/w), alternatively less than 10% (w/w), based on the weight of binder and oxide, of binder. The heterogeneous catalysts comprising binder are commercially available from Clariant International, Ltd.

The heterogeneous catalyst may be in any shape. For example, the heterogeneous catalyst may be in powder, granule, pellet or any extrudate form.

The heterogeneous catalyst may be an oxide of a single element, an oxide of two or more elements, a physical mixture of two or more oxides of different elements, a composite oxide of a single element, or a composite oxide of two or more elements. As used herein, "composite oxide" is intended to mean, but is not limited to, an oxide comprising oxygen in combination with two or more elements and includes crystallite and amorphous composites; composites coated, doped, attached, loaded, or supported with other active components; matrix materials; hybrid composites comprising a matrix material in which one or more of the metal oxide phases is dispersed; and hierarchical porous composites, having pore systems such as micropores, mesopores and macropores.

The heterogeneous catalyst may be made by methods known in the art or purchased from, for example, Sigma Aldrich or Clariant International, Ltd., of Munich, Germany. When the heterogeneous catalyst comprises a binder and/or two or more metal oxides, the metal oxide may be physically mixed with the binder and any other metal oxides by extrusion or other preparation and mixing techniques known in the art. To form a composite heterogeneous catalyst, methods known in the art may also be used, such as an in situ sol-gel hydrolysis or co-precipitation followed by calcination, core-shell growth, intergrowth, overgrowth, or co-crystallization. For example, a composite oxide comprising B and Al may be made according to the procedure described in the examples, where ground $H_3BO_3$, glycerol, ground $Al(NO_3)_3.9 H_2O$ and de-ionized water are combined and heated to 90° C. for 2 hours followed by heating at 150° C. then 400° C. to form the composite.

The methods of the invention may be carried out continuously or be may conducted in batch processes. As used herein, "continuously" means that a stream of organic compound and hydridohalosilane are constantly fed to the reactor containing the heterogeneous catalyst while the organohalosilane product, unreacted organic compound and hydridohalosilane, and any byproducts are removed.

The processes of the invention may be carried out in any reactor suitable for conducting reactions of the type of the invention. For example, the process may be carried out in a batch reactor, such as a sealed tube reactor or autoclave, or in a continuous reactor such as a packed column. Reactors such as tube reactors and packed columns are available commercially. For example, sealed tube reactors and autoclaves may be purchased from the Parr Instrument Company, having offices in Moline, Ill. Other manufactures of suitable pressure reactors include High Pressure Equipment Company of Erie, Pa., Parker Autoclave Engineers of Erie Pa., Büchi AG of Uster, Switzerland, Berghof of Eningen, Germany, and Zeyon, Inc., of Erie, Pa.

The process of the invention is carried out at a temperature of at least 100° C., alternative from 100° C. to 300° C., alternatively from 150° C. to 275° C. At temperatures much above 300° C., the metal oxides may become unstable and ineffective as heterogeneous catalysts.

The process of the invention may be carried out at an absolute pressure of at least 590 kPa; alternatively at least 690 kPa; alternatively at least 3500 kPa; alternatively from 4000 to 15,000 kPa; alternatively from 4000 to 11000 kPa; alternatively from 4000 to 9000 kPa; alternatively from 4000 to 6000 kPa; alternatively from 5000 to 12,000 kPa; alternatively from 8000 to 12,000 pKa.

When the process of the invention is carried out in a continuous process, the contact time is between 0.001 s to 100 minutes; alternatively from 1 s to 50 minutes; alternatively from 10 to 30 minutes. As used herein "contact time"

is intended to mean the time for one reactor volume of the reactants (i.e., organic compound and hydridohalosilane) to pass through the reactor charged with catalyst.

The catalyst is typically in a catalytic effective amount with respect to the organic compound and the hydridohalosilane. A catalytic effective amount in reactor for running a continuous process is an amount sufficient to catalyze the reaction between the organic compound and the hydridohalosilane. For example, a catalytic effective amount of catalyst is at least 0.01 mg catalyst/cm$^3$ of reactor volume; alternatively at least 0.5 mg catalyst/cm$^3$ of reactor volume; alternatively from 1 to 10,000 mg catalyst/cm$^3$ of reactor volume, alternatively a catalytic effective amount is from 0.01 to 50 mol %, alternatively from 0.1 to 15 mol %, alternatively from 0.1 to 5 mol %, based on the weight of all reagents in the reactor. One skilled in the art would know how to determine the correct amount of catalysts depending upon whether using a batch or continuous process and the type of reactor being used. For example, in a continuous reaction in a column, the reactor may be filled with catalyst and the reactants passed between the voids in the catalyst.

There is no required order of addition for the reaction when a batch process is used. In a continuous process the hydridohalosilane and the organic compound are typically contacted together in the presence of the heterogeneous catalyst. For example, the organic compound and the hydridosilane are mixed and flowed together over the heterogeneous catalyst in a continuous reaction.

The molar ratio of organic compound to hydridohalosilanes is typically from 0.5 to 10; alternatively from 0.5 to 4; alternatively from 1 to 4.

The heterogeneous catalyst may be treated with an acid prior to the reacting of the organic compound and the hydridohalosilanes. The acid may be any acid that will reduce the quantity of hydroxyl groups on the surface and remove moisture. In one embodiment, the catalyst is treated with acid prior to the reacting taking place in the process.

Examples of acids that may be used to treat the heterogeneous catalyst include, but are not limited to, halosilanes, mixtures of halosilanes, hydrogen chloride and mixtures of hydrogen chloride and halosilanes. Alternatively the heterogeneous catalyst is treated with HCl. Examples of halosilanes to treat the heterogeneous catalyst include chlorosilane, such as dichlorosilane, trichlorosilane, tetrachlorosilane, phenyltrichlorosilane, methyltrichlorosilane, dimethyldichlorosilane, trimethylchlorosilane, methylchlorosilane, and dimethylchlorosilane. Hydrogen chloride and halosilanes are available commercially or may be produced using methods known the art. The definition of halosilanes as used herein is intended to include halosilanes alone, alkylhalosilanes alone, or combinations of halosilanes and alkylhalosilanes.

The heterogeneous catalyst may be treated with the acid by means known in the art for treating a catalyst with HCl or a halosilane. For example, the heterogeneous catalyst may be treated by flowing hydrogen chloride, halosilanes, a mixture of halosilanes, or a mixture of HCl and a halosilane over the heterogeneous catalyst at between 60° C. and 300° C., alternatively between 100° C. and 200° C. Alternatively, the heterogeneous catalyst is treated with the hydridohalosilane described above for reacting with the organic compound by starting the flow of the hydridohalosilanes in a continuous process prior to the flow of the organic compound at a temperature from 100° C. to 300° C., alternatively from 150° C. to 275° C. One skilled in the art would know how to treat a heterogeneous catalyst with acid according to the invention.

The organohalosilane produced according to the invention may be recovered, after the reaction, from the crude reaction product. As used herein, "crude reaction product" means the mixture containing the organohalosilane prior to any subsequent processing to recover or purify the organohalosilane. Examples of methods of recovering the organohalosilane include, but are not limited to, filtration and distillation. One skilled in the art would know how to filter and distill the organohalosilane produced according to the invention.

The method of the invention produces a crude reaction product comprising the organohalosilane. The organohalosilane produced according to the invention has the formula $R'_p R_n SiH_m X_{4-m-n-p}$, where R and X are as defined above for the hydridohalosilane; each R' is independently $C_1$-$C_{14}$ hydrocarbyl or halogen-substituted hydrocarbyl, p is 1 or 2, alternatively 1, n is 0, 1, or 2, alternatively 1 or 2, alternatively 1; m is 0, 1, or 2, alternatively 0 or 1, alternatively 0; and m+n+p=1, 2 or 3, alternatively 1 or 2, alternatively 2.

The hydrocarbyl groups and halogen-substituted hydrocarbyl groups represented by R' typically have from 1 to 14 carbon atoms, alternatively from 1 to 10 carbon atoms, alternatively from 1 to 6 carbon atoms, alternatively 6 carbon atoms. Examples of the hydrocarbyl groups are those formed by the removal of a hydrogen atom from the organic compound described above. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, decyl, undecyl, dodecyl, tridecyl, and tetradecyl; cycloalkyl, such as cyclopentyl, cyclohexyl, and methylcyclohexyl; alkenyl, such as propenyl, butenyl, pentenyl, hexenyl, heptenyl, octenyl, nonenyl, decenyl, undecenyl, dodecenyl, tridecenyl, and tetradecenyl, cycloalkenyl, such as cyclohexenyl, cyclooctenyl, cyclodecenyl, and cyclododecenyl, aryl, such as phenyl, and naphthyl; alkaryl, such as tolyl, and xylyl; and aralkyl such as benzyl and phenylethyl, and their isomers. The hydrocarbyl groups represented by R' may be halogen-substituted. Examples of halogen-substituted hydrocarbyl groups represented by R' include those defined above for R' with a halogen, such as chlorine, bromine, or iodine substituted for a hydrogen atom of the hydrocarbyl group.

Examples of organohalosilanes produced according to the invention include, but are not limited to, trichloro(methyl) silane, trichloro(ethyl)silane, trichloro(propyl)silane, trichloro(butyl)silane, trichloro(pentyl)silane, trichloro(octyl)silane, trichloro(tetradodecyl)silane, trichloro(chloromethyl)silane, trichloro(2-chloroethyl)silane, trichloro-(3-chloropropyl)silane, trichloro-(4-chlorobutyl)silane, trichloro(cyclohexyl)silane, trichloro-(3-chlorocyclohexyl) silane, trichloro(phenyl)silane, trichloro(naphthyl)silane, trichloro(3-chlorophenyl)silane, trichloro(4-chloronaphthyl) silane, trichloro(tolyl)silane, xytyltrichlorosilane, dichloro (dimethyl)silane, dichloro(ethyl)methylsilane, dichloro(methyl)propylsilane, dichloro(butyl)methylsilane, dichloro (methyl)pentylsilane, dichloro(methyl)octylsilane, dichloro (tetradodecyl)methylsilane, dichloro(chloromethyl) methylsilane, 2-dichloro(chloroethyl)methylsilane, dichloro (3-chloropropyl)methylsilane, 4-dichloro(chlorobutyl) methylsilane, dichloro(cyclohexyl)methylsilane, dichloro(3-chlorocyclohexyl)methylsilane, dichloro(phenyl) methylsilane, dichloro(naphthyl)methylsilane, dichloro (xylyl)methylsilane dichloro(m-chlorophenyl)methylsilane, dichloro(4-chloronaphthyl)methylsilane, dichloro(chlorotolyl)methylsilane, dichloro(chloroxylyl)methylsilane, diethyldichlorosilane, dipropyldichlorosilane, dibutyldichlorosilane, dipentyldichlorosilane, dichloromethyldichlorosilane, bis-(2-chloroethyl)dichlorosilane, bis-(3-chloropropyl)dichlorosilane, dihexyldichlorosilane, dicyclohexyldichlorosilane, bis-(3-chlorocyclohexyl)dichlorosilane, diphenyldichlorosilane, dinaphthyldichlorosilane, bis-(3-chlorophenyl)dichlorosilanes, bis-(4-chloronaphthyl)dichlorosilanes, chloro(trimethyl)silane, chloro(triethyl)silane, chloro(tripropyl)silane, chloro(tributyl)silane, chloro(tripentyl)silane, chloro(trihexyl)silane, chloro(triheptyl)silane, chloro(trioctyl)silane, chloro(trinonyl)silane, chloro(tridodecyl)silane, chloro(tritetradodecyl)silane, tris(chloromethyl)chlorosilane, tris(2-chloroethyl)chlorosilane, tris(3-chloropropyl)chlorosilane, tris(4-chlorobutyl)chlorosilane, (tricyclohexyl)chlorosilane, tris(3-methylcyclohexyl)chlorosilane, tris(3-chlorocyclohexyl)chlorosilane, chloro(triphenyl)silane, chloro(trinaphthyl)silane, tris(3-chlorophenyl)chlorosilane, tris-(chloronaphthyl)chlorosilane, chloro(diethyl)methylsilane, chloro(methyl)dipropylsilane, chloro(dibutyl)methylsilane, chloro(methyl)dipentylsilane, chloro(methyl)dioctylsilane, chloro(ditetradodecyl)methylsilane, chloro(bis-chloromethyl)methylsilane, chloro(bis-2-chloroethyl)methylsilane, chloro(bis-3-chloropropyl)methylsilane, chloro(bis-4-chlorobutyl)methylsilane, chloro(cyclohexyl)methylsilane, chloro(bis-3-chlorocyclohexyl)methylsilane, chloro(diphenyl)methylsilane, chloro(methyl)dinaphthylsilane, chloro(dixylyl)methylsilane chloro(di-m-chlorophenyl)methylsilane, bis-4-chloronaphthyl(chloro)methylsilane, chloro(dichlorotolyl)methylsilane, chloro(dichloroxylyl)methylsilane.

In one embodiment, the crude reaction product comprises less than 50 ppm $BCl_3$ or $AlCl_3$; alternatively no detectable amounts of $BCl_3$ or $AlCl_3$ are in the crude reaction product; alternatively the method includes the proviso that no $BCl_3$ or $AlCl_3$ are added in the method, alternatively with the proviso that less than 50 ppm $BCl_3$ or $AlCl_3$ are reacted in the method. $BCl_3$ and $AlCl_3$ are to be avoided in the method of the invention since $BCl_3$ and $AlCl_3$ are harder to remove from the crude reaction product and may catalyze the formation of byproducts in later processing. This issue reduces a benefit of using the heterogeneous catalyst, which is easy separation of the catalyst before subsequent processing steps.

The method of the invention produces organohalosilanes at lower pressure and temperature, with better yields, with fewer byproducts, and more economically than known processes. In addition, the method employs a heterogeneous catalyst that can be easily removed from the crude reaction product.

The organohalosilane products of the present method are used as precursors to make many different commercial products including arylsiloxanes which also have many commercial uses.

EXAMPLES

The invention is further illustrated by, and an invention embodiment may include any combinations of features and limitations of, the non-limiting examples thereof that follow.

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute modes for its practice. However, those of skill in the art should, in light of the present disclosure, appreciate that many changes can be made in the specific embodiments which are disclosed and still obtain a like or similar result without departing from the spirit and scope of the invention. Unless otherwise indicated, all percentages are in weight % (wt. %). When the unit 'parts per million' (ppm) are used in the example, it is based on weight. The following table describes the abbreviations used in the examples:

TABLE 1A

List of abbreviations used in the examples.

| Abbreviation | Word |
| --- | --- |
| G, gr, or g | gram |
| Me | methyl |
| Wt. | weight |
| % | percent |
| TCD | Thermal conductivity detector |
| MS | Mass spectroscopy |
| GC | Gas chromatography |
| psi | pounds per square inch |
| kPa | kilopascals |
| Mol | mole |
| Y | gamma |
| hr | hour |
| ° C. | degrees Celsius |
| NA | Not Applicable |
| mm | millimeters |
| mL | Milliliters |
| cm | Centimeter |
| " | Inch (with 1" = 2.54 centimeters) |
| CS331-1 | ⅛" extrusion, 200-300 $m^2/g$, γ-Alumina from Sud-Chemie Inc. |
| CS331-3 | ⅛" extrusion, 200-300 $m^2/g$, γ-Alumina from Sud-Chemie Inc. |
| CS331-4 | ⅛" extrusion, 175-275 $m^2/g$, γ-Alumina from Sud-Chemie Inc. |
| CS331-4B | 1/10" CDS extrusion, 175-275 $m^2/g$, γ-Alumina from Sud-Chemie Inc. |
| CS331-5 | 1/10" CDS extrusion, 200-300 $m^2/g$, γ-Alumina from Sud-Chemie Inc. |
| CS331-9 | 1/16" CDS extrusion, 175-300 $m^2/g$, α/γ-Alumina from Sud-Chemie Inc. |
| CS308 | ⅛" extrusion, 180-250 $m^2/g$, Alumina from Sud-Chemie Inc. |
| CS501 (T2555) | ⅛" extrusion, 250-350 $m^2/g$, Alumina from Sud-Chemie Inc. |

TABLE 1A-continued

List of abbreviations used in the examples.

| Abbreviation | Word |
| --- | --- |
| CS601 (T2555) | ⅛" extrusion, 140-150 m²/g, η-Alumina from Sud-Chemie Inc. |
| CS332 | 1/16" extrusion, 200-300 m²/g, γ-Alumina from Sud Chemie Inc. |
| CS332HT | 1/20" CDS Extrusion, <8.0 m²/g, α-Alumina from Sud-Chemie Inc. |
| C04-NAAC-18 | α-Alumina Nanosheet, aspect ratio 10-200, from Sawyer Technical Materials. |
| C18-NAAC-7 | α-Alumina/Boehmite Nanosheet, Aspect Ratio 50-200, from Sawyer Technical Materials |
| Boria | $B_2O_3$ |
| Alumina | $Al_2O_3$ - unless specified, refers to γ-alumina |
| Zirconium Oxide | $ZrO_2$ |
| XZO 1501/23 | High Porosity zirconium oxide calcined at 500° C. from MEL Chemicals |
| XZO 1715/04 | Sulphated zirconium oxide from MEL Chemicals |
| XZO 2056/02 | Tungstated zirconium oxide from MEL Chemicals |
| PP-8015 | 1/16" extrusion, zirconia with alumina binder from Sud Chemie |

Method of Creating Alumina/Boria Catalyst 1.91 gr. $H_3BO_3$ (pre-ground with a mortar and pestle) was added to a porcelain dish along with 6.83 gr. of glycerol and stirred with a spatula until a consistent paste was obtained (5-10 minutes). 65.63 gr. $Al(NO_3)_3.9\ H_2O$ (pre-ground with a mortar and pestle) was then added and the mixture stirred for two minutes. 4.08 gr. of de-ionized water was added and stirred until a consistent paste was obtained. The dish was then heated on a hotplate and heated to 90° C., at which point yellow vapors (nitrates) were observed. Heating was continued for 2 hours to drive off water as well as nitrates. The dish was then placed in an air circulating oven at 150° C. for 2 hours. When removed from the oven the material was a yellow, puffy, solid. The dish was then placed in an air circulating oven at 400° C. overnight. The resulting catalyst was 15% (w/w) boria and 85% (w/w) alumina. The other catalysts comprising alumina and boria were prepared using the same method except the amount of reagents were varied to provide the percentages of boria and alumina described in the examples.

Analysis by GC

Analysis was conducted using HP 5890 and HP 6890 gas chromatographs (GC's) equipped with a thermal conductivity detector (TCD) and a 30 meter DB-210 column with an internal diameter of 0.25 mm and a film thickness of 0.50 μm.

Catalyst and Reactant Preparation Prior to Use in the Examples:

All reactant mixtures were prepared in a $N_2$ purged glovebag. Catalyst samples were prepared by drying in flowing $N_2$ at 300-400° C. overnight. The catalyst samples were transferred while still warm and under $N_2$ purge to vials and sealed. The vials containing catalyst were then transferred to a desiccator in a $N_2$ purged glovebag. Prior to use the vials for transferring catalyst were dried in an air circulated oven at 150° C. overnight and removed from the oven just prior to use.

Experimental Procedure Used in Examples

Catalysts and reactant mixtures were loaded into glass tubes, sealed on one end in a $N_2$ purged glovebag and temporarily sealed on the other end using a rubber setpa. The tubes comprised 1% (w/w) of catalyst if liquid, based on the weight of catalyst and all other reactants, and a consistent visual amount (approximately 1% (w/w) based on the weight of the catalyst and reactants) if solid. The loaded tubes, sealed with rubber septa's were then removed from the glovebag and sealed with a glass torch on the open end, below the rubber stopper. The sealed glass tubes containing reactant and catalyst were then heated in a metal heating block at a given temperature and time to carry out the reaction. Once removed from the heating block the tubes were cooled first at room temperature and then in a dry-ice/acetone bath. While cold the tubes were cracked open and temporarily sealed with a rubber septa until the reaction mixture was completely thawed. Once thawed, the reaction products were transferred from the glass tube reactor to a vial for analysis. Pressures reported in glass tubes are absolute; for continuous runs, they are gauge pressures.

Example 1

A mixture containing a 2:1 molar ratio of benzene to methydichlorosilane was placed in a series of glass tubes, each with catalyst comprising 20% boria/80% alumina and a graphite binder, and the tubes sealed. The tubes were heated to 250° C., at an estimated internal pressure of 10,342 kPa, for the times given in Table 1B. At the indicated time, the tubes were cooled and the contents analyzed by GC-TCD. The results are presented as percent area under the curve (GC-TCD Area %), as defined by GC-TCD analysis.

TABLE 1B

20% Boria/80% Alumina - Graphite Binder Catalyzed Reaction of Benzene with Methyldichlorosilane

| Time | GC-TCD Area Percent | | | |
| --- | --- | --- | --- | --- |
| Min. | MeHSiCl2 | MeSiCl3 | Benzene | PhMeSiCl2 |
| 0 | 36.93 | 0.00 | 60.65 | 0.00 |
| 60 | 33.80 | 0.40 | 63.20 | 1.28 |
| 120 | 16.90 | 2.30 | 58.81 | 8.04 |
| 180 | 16.96 | 5.13 | 53.38 | 17.25 |
| 240 | 9.35 | 6.74 | 46.88 | 25.44 |

Example 2

A mixture containing a 2:1 molar ratio of benzene to methydichlorosilane was placed in a series of glass tubes, each with 15% boria/85% alumina with a graphite binder catalyst, and the tubes sealed. The tubes were heated to 250° C., at an estimated internal pressure of 10,342 kPa, for the times given in Table 2. At the indicated time, the tubes were cooled and the contents analyzed by GC-TCD. The results are presented as percent area under the curve, as defined by GC-TCD analysis.

TABLE 2

15% Boria/85% Alumina - Graphite Binder Catalyzed Reaction of Benzene with Methyldichlorosilane

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 8.51 | 1.80 | 59.49 | 6.47 |
| 90 | 5.16 | 3.12 | 54.89 | 19.46 |
| 120 | 13.95 | 6.52 | 50.56 | 19.32 |
| 180 | 8.26 | 9.68 | 52.18 | 19.24 |
| 240 | 7.58 | 0.79 | 49.22 | 19.05 |

Example 3

A mixture containing a 2:1 molar ratio of benzene to methyldichlorosilane was placed in a series of glass tubes, each with 20% boria/80% alumina with an aluminum stearate binder catalyst, and the tubes sealed. The tubes were heated to 250° C., at an estimated internal pressure of 10,342 kPa, for the times given in Table 3. At the indicated time, the tubes were cooled and the contents analyzed by GC-TCD. The results are presented as percent area under the curve, as defined by GC-TCD analysis.

TABLE 3

20% Boria/80% Alumina - Aluminum Stearate Binder Catalyzed Reaction of Benzene with Methyldichlorosilane

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 34.60 | 0.59 | 62.16 | 1.21 |
| 90 | 32.52 | 1.02 | 61.39 | 3.00 |
| 120 | 23.06 | 3.19 | 58.51 | 10.39 |
| 180 | 14.80 | 6.32 | 55.05 | 15.90 |
| 240 | 9.00 | 7.51 | 51.97 | 20.70 |

Example 4

A mixture containing a 2:1 molar ratio of benzene to methyldichlorosilane was placed in a series of glass tubes, each with CS331-1 alumina catalyst, and the tubes sealed. The tubes were heated to 250° C., at an estimated internal pressure of 10,342 kPa, for the times given in Table 4. At the indicated time, the tubes were cooled and the contents analyzed by GC-TCD. The results are presented as percent area under the curve, as defined by GC-TCD analysis.

TABLE 4

CS331-1 Alumina Catalyzed Reaction of Benzene with Methyldichlorosilane

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 31.29 | 1.66 | 63.90 | 0.40 |
| 90 | 28.38 | 3.04 | 63.83 | 0.84 |
| 180 | 20.51 | 7.12 | 63.03 | 2.63 |
| 240 | 19.74 | 7.18 | 63.93 | 2.87 |

Example 5

A mixture containing a 2:1 molar ratio of benzene to methyldichlorosilane was placed in a series of glass tubes, each with CS331-3 alumina catalyst, and the tubes sealed. The tubes were heated to 275° C., at an estimated internal pressure of 10,342 kPa, for the times given in Table 5. At the indicated time, the tubes were cooled and the contents analyzed by GC-TCD. The results are presented as percent area under the curve, as defined by GC-TCD analysis.

TABLE 5

CS331-3 Alumina Catalyzed Reaction of Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 27.69 | 3.21 | 63.85 | 1.24 |
| 90 | 23.44 | 5.15 | 63.89 | 1.96 |
| 120 | 20.84 | 6.83 | 63.30 | 2.67 |
| 180 | 17.03 | 8.96 | 62.90 | 3.98 |
| 240 | 13.63 | 10.54 | 60.53 | 7.52 |

Example 6

A mixture containing a 2:1 molar ratio of benzene to methyldichlorosilane was placed in a series of glass tubes, each with CS331-4 alumina catalyst, and the tubes sealed. The tubes were heated to 250° C., at an estimated internal pressure of 10,342 kPa, for the times given in Table 6. At the indicated time, the tubes were cooled and the contents analyzed by GC-TCD. The results are presented as percent area under the curve, as defined by GC-TCD analysis.

TABLE 6

CS331-4 Alumina Catalyzed Reaction of Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 23.95 | 6.57 | 62.65 | 2.06 |
| 90 | 18.94 | 9.52 | 61.90 | 3.73 |
| 120 | 17.90 | 10.22 | 61.33 | 3.99 |
| 180 | 14.35 | 11.78 | 60.71 | 5.36 |
| 240 | 11.23 | 12.76 | 60.67 | 6.64 |

Example 7

A mixture containing a 2:1 molar ratio of benzene to methyldichlorosilane was placed in a series of glass tubes, each with CS331-5 alumina catalyst, and the tubes sealed. The tubes were heated to 250° C., at an estimated internal pressure of 10,342 kPa, for the times given in Table 7. At the indicated time, the tubes were cooled and the contents analyzed by GC-TCD. The results are presented as percent area under the curve, as defined by GC-TCD analysis.

TABLE 7

CS331-5 Alumina Catalyzed Reaction of
Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 34.24 | 0.27 | 55.72 | 3.98 |
| 120 | 32.43 | 0.45 | 53.83 | 6.79 |
| 180 | 29.99 | 0.69 | 52.95 | 9.73 |
| 240 | 29.86 | 0.70 | 53.17 | 9.60 |

Example 8

A mixture containing a 2:1 molar ratio of benzene to methydichlorosilane was placed in a series of glass tubes, each with CS331-4B alumina catalyst, and the tubes sealed. The tubes were heated to 250° C., at an estimated internal pressure of 10,342 kPa, for the times given in Table 8. At the indicated time, the tubes were cooled and the contents analyzed by GC-TCD. The results are presented as percent area under the curve, as defined by GC-TCD analysis.

TABLE 8

CS331-4B Alumina Catalyzed Reaction
of Benzene with Methyldichlorosilane

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 31.81 | 1.60 | 63.59 | 0.14 |
| 90 | 28.40 | 3.69 | 63.20 | 0.80 |
| 120 | 28.63 | 3.58 | 62.89 | 1.02 |
| 180 | 22.75 | 6.64 | 63.32 | 2.07 |
| 240 | 20.48 | 7.98 | 62.62 | 3.07 |

Example 9

A mixture containing a 2:1 molar ratio of benzene to methydichlorosilane was placed in a series of glass tubes, each with CS331-9 alumina catalyst, and the tubes sealed. The tubes were heated to 275° C., at an estimated internal pressure of 10,342 kPa, for the times given in Table 9. At the indicated time, the tubes were cooled and the contents analyzed by GC-TCD. The results are presented as percent area under the curve, as defined by GC-TCD analysis.

TABLE 9

CS331-9 Alumina Catalyzed Reaction of
Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 25.12 | 3.75 | 63.48 | 1.10 |
| 90 | 24.67 | 5.62 | 63.57 | 0.29 |
| 120 | 18.36 | 9.24 | 63.04 | 1.83 |
| 180 | 16.55 | 10.02 | 62.40 | 3.73 |
| 240 | 15.89 | 9.79 | 62.20 | 5.12 |

Example 10

A mixture containing a 2:1 molar ratio of benzene to methydichlorosilane was placed in a series of glass tubes, each with CS332 alumina catalyst, and the tubes sealed. The tubes were heated to 275° C., at an estimated internal pressure of 10,342 kPa, for the times given in Table 10. At the indicated time, the tubes were cooled and the contents analyzed by GC-TCD. The results are presented as percent area under the curve, as defined by GC-TCD analysis.

TABLE 10

CS332 Alumina Catalyzed Reaction of
Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 22.35 | 3.97 | 65.75 | 0.38 |
| 90 | 21.60 | 4.58 | 65.69 | 0.28 |
| 120 | 17.46 | 7.77 | 67.14 | 0.24 |
| 180 | 15.67 | 8.15 | 64.79 | 3.99 |
| 240 | 13.83 | 8.29 | 63.79 | 6.06 |

Example 11

A mixture containing a 2:1 molar ratio of benzene to methydichlorosilane was placed in a series of glass tubes, each with CS308 alumina catalyst, and the tubes sealed. The tubes were heated to 275° C., at an estimated internal pressure of 10,342 kPa, for the times given in Table 11. At the indicated time, the tubes were cooled and the contents analyzed by GC-TCD. The results are presented as percent area under the curve, as defined by GC-TCD analysis.

TABLE 11

CS308 Alumina Catalyzed Reaction of
Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 24.32 | 4.90 | 62.62 | 1.91 |
| 90 | 20.20 | 6.99 | 62.72 | 2.98 |
| 120 | 18.86 | 8.10 | 62.15 | 4.08 |
| 180 | 16.37 | 9.33 | 61.75 | 5.41 |
| 240 | 16.38 | 9.33 | 61.51 | 4.78 |

Example 12

A mixture containing a 2:1 molar ratio of benzene to methydichlorosilane was placed in a series of glass tubes, each with CS501 (T-2555) alumina catalyst, and the tubes sealed. The tubes were heated to 275° C., at an estimated internal pressure of 10,342 kPa, for the times given in Table 12. At the indicated time, the tubes were cooled and the contents analyzed by GC-TCD. The results are presented as percent area under the curve, as defined by GC-TCD analysis.

TABLE 12

CS501 (T-2555) Alumina Catalyzed Reaction of Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 18.45 | 3.29 | 69.66 | 1.07 |
| 90 | 14.87 | 6.39 | 69.37 | 1.14 |
| 120 | 13.12 | 8.04 | 69.07 | 1.43 |
| 180 | 8.97 | 10.53 | 70.86 | 1.29 |
| 240 | 8.02 | 12.13 | 70.19 | 1.35 |

Example 13

A mixture containing a 2:1 molar ratio of benzene to methyldichlorosilane was placed in a series of glass tubes, each with CS601 (T-2555) alumina catalyst, and the tubes sealed. The tubes were heated to 275° C., at an estimated internal pressure of 10,342 kPa, for the times given in Table 13. At the indicated time, the tubes were cooled and the contents analyzed by GC-TCD. The results are presented as percent area under the curve, as defined by GC-TCD analysis.

TABLE 13

CS601 (T-2555) Alumina Catalyzed Reaction of Benzene with Methyldichlorosilane

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 24.89 | 0.67 | 68.51 | 0.11 |
| 90 | 24.18 | 0.89 | 68.31 | 0.08 |
| 120 | 10.83 | 5.75 | 65.45 | 1.35 |
| 180 | 15.49 | 1.15 | 69.18 | 0.65 |
| 240 | 19.20 | 2.10 | 69.70 | 0.22 |

Example 14

A mixture containing a 2:1 molar ratio of benzene to methyldichlorosilane was placed in a series of glass tubes, each with 0.5% platinum on alumina catalyst, and the tubes sealed. The tubes were heated to 275° C., at an estimated internal pressure of 10,342 kPa, for the times given in Table 14. At the indicated time, the tubes were cooled and the contents analyzed by GC-TCD. The results are presented as percent area under the curve, as defined by GC-TCD analysis.

TABLE 14

Platinum (0.5% (w/w)) on Alumina Catalyzed Reaction of Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 17.64 | 6.48 | 68.20 | 0.17 |
| 90 | 12.44 | 8.41 | 67.02 | 3.76 |
| 120 | 10.75 | 12.34 | 67.20 | 1.77 |
| 180 | 10.59 | 13.76 | 67.52 | 0.27 |
| 240 | 22.03 | 7.41 | 65.30 | 1.81 |

Example 15

A mixture containing a 2:1 molar ratio of benzene to methyldichlorosilane was placed in a series of glass tubes, each with CS332HT alumina catalyst, and the tubes sealed. The tubes were heated to 275° C., at an estimated internal pressure of 10,342 kPa, for the times given in Table 15. At the indicated time, the tubes were cooled and the contents analyzed by GC-TCD. The results are presented as percent area under the curve, as defined by GC-TCD analysis.

TABLE 15

CS332HT Alumina Catalyzed Reaction of Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 34.23 | 0.32 | 64.33 | 0.00 |
| 90 | 33.62 | 0.43 | 64.88 | 0.04 |
| 120 | 36.44 | 0.44 | 62.17 | 0.04 |
| 180 | 35.27 | 0.90 | 62.08 | 0.25 |
| 240 | 33.20 | 1.51 | 62.25 | 0.77 |

Example 16

A mixture containing a 2:1 molar ratio of benzene to methyldichlorosilane was placed in a series of glass tubes, each with α-Alumina/Boehmite Nanosheet (C18-NAAC-7) catalyst, and the tubes sealed. The tubes were heated to 275° C., at an estimated internal pressure of 10,342 kPa, for the times given in Table 16. At the indicated time, the tubes were cooled and the contents analyzed by GC-TCD. The results are presented as percent area under the curve, as defined by GC-TCD analysis.

TABLE 16

α-Alumina/Boehmite Nanosheet (C18-NAAC-7) Catalyzed Reaction of Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 37.38 | 0.06 | 61.56 | 0.03 |
| 90 | 37.05 | 0.11 | 62.23 | 0.00 |
| 120 | 37.60 | 0.09 | 61.79 | 0.02 |
| 180 | 36.81 | 0.25 | 62.25 | 0.02 |
| 240 | 37.14 | 0.39 | 61.79 | 0.02 |

Example 17

A mixture containing a 2:1 molar ratio of benzene to methyldichlorosilane was placed in a series of glass tubes, each with 100% α-Alumina Nanosheets (C04-NAAC-18) catalyst, and the tubes sealed. The tubes were heated to 275° C., at an estimated internal pressure of 10,342 kPa, for the times given in Table 17. At the indicated time, the tubes were cooled and the contents analyzed by GC-TCD. The results are presented as percent area under the curve, as defined by GC-TCD analysis.

TABLE 17

100% α-Alumina Nanosheets (C04-NAAC-18) Catalyzed
Reaction of Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 37.29 | 0.07 | 62.03 | 0.03 |
| 90 | 16.99 | 0.08 | 81.48 | 0.04 |
| 120 | 36.46 | 0.14 | 62.71 | 0.00 |
| 180 | 33.36 | 0.13 | 65.87 | 0.02 |
| 240 | 37.32 | 0.26 | 61.89 | 0.03 |

Example 18

A mixture containing a 2:1 molar ratio of benzene to methyldichlorosilane was placed in a series of glass tubes, each with a high porosity zirconium oxide (MEL Chemicals XZO 1501/23) catalyst, and the tubes sealed. The tubes were heated to 250° C., at an estimated internal pressure of 10,342 kPa, for the times given in Table 18. At the indicated time, the tubes were cooled and the contents analyzed by GC-TCD. The results are presented as percent area under the curve, as defined by GC-TCD analysis.

TABLE 18

High Porosity Zirconium Oxide (MEL Chemicals XZO 1501/23)
Catalyzed Reaction of Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 32.00 | 0.81 | 64.53 | 0.15 |
| 90 | 27.87 | 2.05 | 63.94 | 2.18 |
| 120 | 26.63 | 2.35 | 63.38 | 2.87 |
| 180 | 20.92 | 4.50 | 59.72 | 7.57 |
| 240 | 18.44 | 5.32 | 60.02 | 8.69 |

Example 19

A mixture containing a 2:1 molar ratio of benzene to methyldichlorosilane was placed in a series of glass tubes, each with a sulphated zirconium oxide (MEL Chemicals XZO 1715/04) catalyst, and the tubes sealed. The tubes were heated to 250° C., at an estimated internal pressure of 10,342 kPa, for the times given in Table 19. At the indicated time, the tubes were cooled and the contents analyzed by GC-TCD. The results are presented as percent area under the curve, as defined by GC-TCD analysis.

TABLE 19

Sulphated Zirconium Oxide (XZO 1715/04) Catalyzed
Reaction of Benzene with Methyldichlorosilane

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 17.53 | 2.69 | 68.46 | 1.73 |
| 120 | 14.13 | 3.78 | 68.06 | 2.68 |
| 180 | 11.35 | 4.35 | 70.34 | 3.77 |
| 240 | 11.35 | 4.40 | 69.47 | 4.18 |

Example 20

A mixture containing a 2:1 molar ratio of benzene to methyldichlorosilane was placed in a series of glass tubes, each with a tungstated zirconium oxide (MEL Chemicals XZO 2056/02) catalyst, and the tubes sealed. The tubes were heated to 250° C., at an estimated internal pressure of 10,342 kPa, for the times given in Table 20. At the indicated time, the tubes were cooled and the contents analyzed by GC-TCD. The results are presented as percent area under the curve, as defined by GC-TCD analysis.

TABLE 20

Tungstated Zirconium Oxide (XZO 2056/02) Catalyzed
Reaction of Benzene with Methyldichlorosilane

| Time | GC-TCD Area Percent | | | |
|---|---|---|---|---|
| Min. | MeHSiCl2 | MeSiCl3 | Benzene | PhMeSiCl2 |
| 0 | 36.93 | 0 | 60.65 | 0 |
| 60 | 19.74 | 9.78 | 65.89 | 0.48 |
| 120 | 14.56 | 13.27 | 66.84 | 0.88 |
| 180 | 15.16 | 13.54 | 66.11 | 0.78 |
| 240 | 15.20 | 13.12 | 66.29 | 0.71 |

Example 21

In a fixed bed reactor having a 0.95 cm inner diameter was loaded 3.0 gr of crushed Clariant, CS331-4, activated alumina. The catalyst material was held in place on both ends of the reactor with a layer of glass wool and 5 gr. of 3 mm borosilicate glass beads. The catalyst was dried by flowing He through the reactor and maintaining the temperature of the catalyst bed at 300° C. for 4 hours.

Table 21 below contains the results for PhMeSiCl$_2$ formation for a series of five 8-hour runs performed at various pressures, using the same catalyst bed, with a constant reactor temperature of 250° C. with a 2:1 molar ratio of benzene to MeHSiCl$_2$ as a feed mixture. At the end of each run, the system was flushed with dry benzene, cooled down, and maintained under a dry nitrogen environment until the next run. The liquid feed rate to the reactor system was 5 ml/min. The feed was passed through a pre-heater prior to the fixed bed reactor itself. The fixed bed reactor has heated as needed to maintain a 250° C. temperature within the catalyst bed.

TABLE 21

Run Results at Varous Pressures in a Packed
Bed Reactor with Activated Alumina Catalyst.

| Run # | System Pressure (psig) | PhMeSiCl$_2$ Yield (GC-TCD Area %) |
|---|---|---|
| 1 | 1200 | 2.00 |
| 2 | 500 | 1.97 |
| 3 | 225 | 0.98 |
| 4 | 625 | 1.59 |
| 5 | 1200 | 1.95 |

Example 22

A fixed bed reactor was constructed with a 5.08 cm inner diameter with a 91.44 cm length heated length between the flanges. The feed material was pre-heated prior to being fed into the fixed bed reactor. The typical feed rate to the system was 20 ml/min and this resulted in a residence time in the catalyst bed of about 17 minutes.

The reactor was packed from bottom to top with 7.62 cm of borosilicate glass beads followed by 91.44 cm of Clariant CS-331-1, ⅛" γ-alumina extrudate and then an additional 7.62 cm of borosilicate glass beads. The catalyst bed was then dried overnight by flowing $N_2$ through the reactor from bottom to top at a flow-rate of 100 ml/min while maintaining a reactor temperature of 400° C.

The feed mixture to the reactor consisted of a 2:1 molar ratio of benzene to $MeHSiCl_2$. The feed rate was 20 ml/min. The system was equipped with an on-line GC system that sampled the crude reactor product leaving the reactor every 30 minutes for GC analysis using a TCD detector. The reactor was operated for 16 hours at 250° C. and 8274 kPa±69 kPa. The amount of $PhMeSiCl_2$ was 3.0±0.2 GC TCD Area % in the crude reactor product samples taken during this portion of the run.

The reactor temperature was increased to 270° C. and the run continued for an additional 8 hours with samples of the crude product taken every 30 minutes. The crude product samples collected during this period contained 7.5±0.3 GC TCD Area %.

Example 23

Several kg of heterogeneous catalyst comprising a composite of boria alumina with a molar ratio of B to Al of 1 to 4 were prepared using the procedure "Method of Creating Alumina/Boria Catalyst" above. This heterogeneous catalyst material was tested in a fixed bed reactor as a 0.32×0.32 cm tablet form produced using either a graphite or aluminum stearate binder. The reactor system was that the same as that described in Example 22.

A run was performed with the 0.32×0.32 cm tablets produced using an aluminum stearate binder. The reactor was loaded with 26 cm of borosilicate glass beads and a layer of glass wool, followed by 25 cm of the catalyst tablets, and then a layer of glass wool and an additional 51 cm of glass beads. The bed was dried by flowing dry $N_2$ through the bed from bottom to top for 18 hours while maintaining the reactor at 150° C.

The feed mixture was a 1.5 to 1.0 molar ratio of benzene to $MeHSiCl_2$. The reactor was operated at a temperature of 250° C. and 8274 kPa and run for a total of 28 hours. The crude product from the reactor was sampled periodically and analyzed using a GC with a TCD detector. At the beginning of the run the crude product contained 14 GC TCD Area % $PhMeSiCl_2$ and slowly dropped off to about 10 GC TCD Area % after 8 hours and remained relatively steady for the remainder of the run.

Example 24

The same conditions, reactor, parameters and reactants were used in this example as used in Example 23 except were differences are noted. A run as was performed with 0.32×0.32 cm tablets produced using an graphite binder. The reactor was loaded 30 cm of borosilicate glass beads and a layer of glass wool, followed by 41 cm of catalyst tablets, and then a layer of glass wool and an additional 30 cm of glass beads. The bed was dried by flowing dry $N_2$ through the bed from bottom to top for 18 hours while maintaining the reactor at 150° C.

The feed mixture was a 1.53 to 1.0 molar ratio of benzene to $MeHSiCl_2$. The reactor was operated at a temperature of 250° C. and 8274 kPa and run for a total of 26 hours. The crude product from the reactor was sampled hourly and analyzed using a GC with a TCD detector. After the system reached steady state the crude product contained 13.5-14.0 GC TCD Area % $PhMeSiCl_2$. The amount of $PhMeSiCl_2$ gradually decreased over the run. After 20 hours on stream the crude product contained 10.0 GC TCD Area % $PhMeSiCl_2$.

Example 25

Samples of γ-alumina were used as catalyst in the reaction of benzene and $MeHSiCl_2$ in glass tubes. Reactions were conducted using a 2:1 molar ratio of benzene to $MeHSiCl_2$ at 250° C. for 16 hours. The catalyst used in the reactions varied with respect to the treatment of the catalyst prior to the reaction. Two catalyst samples were dried without acid treatment and two samples were dried with acid treatment. The non-acid-treated metal oxide catalyst samples were dried overnight (~16 hours) in flowing He at 300-325° C. The acid-treated metal oxide catalyst were first dried in a flowing 50/50 mixture of He and anhydrous HCl for 4-5 hours at 300-325° C. and then overnight (~16 hours) in flowing He at 300-325° C. The reaction results with the two treatment methods are in Table 22 below. All reaction parameters were the same except for the catalyst treatment prior to use as the catalyst in the reaction. The results demonstrate the improved yield of $PhMeSiCl_2$ with catalyst acid treatment combined with drying compared to drying alone prior to using as catalyst in the reaction of benzene and $MeHSiCl_2$.

TABLE 22

The results are shown in the table below.

| Catalyst | $PhMeSiCl_2$ Yield % |
| --- | --- |
| CS331-3 | 8.63 |
| CS331-3 Acid Treated | 9.62 |
| CS331-4 | 7.48 |
| CS331-4 Acid Treated | 10.54 |

Example 26

A mixture containing a 2:1 molar ratio of cyclohexane to methydichlorosilane was placed in a glass tube reactor with CS-331-4, γ-alumina catalyst. The glass tube reactor was sealed and heated to 275° C., at an estimated internal pressure of 1200 psi, for 16 hours. The tube reactor was then cooled and the contents analyzed by GC-TCD. The crude product mixture contained 19.0 GC-TCD Area % cyclohexylmethyldichlorosilane, verified by gas chromatograph/Mass spectrometer (GC/MS) analysis.

Example 27

A mixture containing a 2:1 molar ratio of cyclohexane to methydichlorosilane was placed in a glass tube reactor with PP-8015, zirconia catalyst. The glass tube reactor was sealed and heated to 275° C., at an estimated internal pressure of 1200 psi, for 16 hours. The tube reactor was then cooled and the contents analyzed by GC-TCD. The crude product mixture contained 15.2 GC-TCD Area % cyclohexylmethyldichlorosilane, verified by GC/MS analysis.

Example 28

A mixture containing a 1.55:1 molar ratio of octene to dimethylchlorosilane was loaded into a series of glass tubes, each with CS331-4 alumina catalyst, and the tubes sealed. The tubes were heated to 150° C., at an estimated internal pressure of 10,342 kPa, for the times given in Table 23, below. At the indicated time, the tubes were cooled and the contents analyzed by GC-TCD. The results are presented as percent area under the curve, as defined by GC-TCD analysis.

TABLE 23

CS331-4 Alumina Catalyzed Reaction of octene with dimethylchlorosilane at 150° C.

| Time | GC-TCD Area Percent | | | |
|---|---|---|---|---|
| Min. | Me2HSiCl | Octene | Me2SiCl2 | (Octyl)Me2SiCl |
| 0 | 30.3 | 68.7 | 0.0 | 0.0 |
| 120 | 13.7 | 38.5 | 14.1 | 20.0 |
| 240 | 3.5 | 24.2 | 7.5 | 58.4 |
| 480 | 0.7 | 20.1 | 5.8 | 64.0 |

Example 29

A mixture containing a 1.55:1 molar ratio of octene to dimethylchlorosilane was loaded into a series of glass tubes, each with CS331-4 alumina catalyst, and the tubes sealed. The tubes were heated to 100° C., at an estimated internal pressure of 10,342 kPa, for the times given in Table 24, below. At the indicated time, the tubes were cooled and the contents analyzed by GC-TCD. The results are presented as percent area under the curve, as defined by GC-TCD analysis.

TABLE 24

CS331-4 Alumina Catalyzed Reaction of octene with dimethylchlorosilane at 100° C.

| Time | GC-TCD Area Percent | | | |
|---|---|---|---|---|
| Min. | Me2HSiCl | Octene | Me2SiCl2 | (Octyl)Me2SiCl |
| 0 | 30.3 | 68.7 | 0.0 | 0.0 |
| 60 | 27.5 | 64.0 | 3.7 | 0.2 |
| 120 | 27.1 | 62.3 | 5.0 | 0.6 |
| 240 | 15.1 | 43.3 | 4.5 | 32.4 |

Example 30

A mixture containing a 1.55:1 molar ratio of octene to dimethylchlorosilane was loaded into a series of glass tubes, each with PP-8015 zirconia catalyst, and the tubes sealed. The tubes were heated to 100° C., at an estimated internal pressure of 10,342 kPa, for the times given in Table 25, below. At the indicated time, the tubes were cooled and the contents analyzed by GC-TCD. The results are presented as percent area under the curve, as defined by GC-TCD analysis.

TABLE 25

PP-8015 Zirconia Catalyzed Reaction of octene with dimethylchlorosilane at 100° C.

| Time | GC-TCD Area Percent | | | |
|---|---|---|---|---|
| Min. | Me2HSiCl | Octene | Me2SiCl2 | (Octyl)Me2SiCl |
| 0 | 30.3 | 68.7 | 0.0 | 0.0 |
| 60 | 28.2 | 65.7 | 0.7 | 1.4 |
| 120 | 26.8 | 66.8 | 0.8 | 1.9 |

That which is claimed is:

1. A method for producing an organohalosilane, the method comprising:
reacting an organic compound comprising a halogen-substituted or unsubstituted alkane, a halogen-substituted or unsubstituted alkene, or an aromatic compound and at least one hydridohalosilane of formula $R_nSiH_mX_{4-m-n}$, wherein each R is independently $C_1$-$C_{14}$ hydrocarbyl or $C_1$-$C_{14}$ halogen-substituted hydrocarbyl, X is fluoro, chloro, bromo, or iodo, n is 0, 1, or 2, m is 1, 2 or 3, and m+n=1, 2 or 3, in the presence of a heterogeneous catalyst comprising an oxide of two or more of the elements Sc, Y, Ti, Zr, Hf, B, Al, Ga, In, C, Si, Ge, Sn, or Pb, at a temperature greater than 100° C., and at a pressure of at least 690 kPa, to produce a crude reaction product comprising the organohalosilane.

2. The method of claim 1 wherein the heterogeneous catalyst comprises alumina, zirconium dioxide, an oxide comprising Zr and B, an oxide comprising Al and B, or an oxide comprising Al and Si.

3. The method as in claim 1, wherein the oxide comprises Al and one of the elements of B, Zr, Ti, or Si; or Zr and one of the elements of B, Ti, or Si.

4. The method as in claim 3, wherein the oxide of two or more elements comprises oxides of formula $Al_9B_2O_{15}$ or $Al_4B_2O_9$.

5. The method of claim 1 wherein the organohalosilane is of the formula $R'_pR_nSiH_mX_{4-m-n-p}$, wherein each R' is independently $C_1$—$O_{14}$ substituted or unsubstituted hydrocarbyl, p is 1 or 2, n is 0, 1, or 2, m is 0, 1, or 2, and m+n+p=1, 2 or 3.

6. The method of claim 1, wherein the organic compound comprises cyclohexane, octene, benzene, toluene, halobenzene, dihalobenzene, naphthalene, or halonaphthalene.

7. The method of claim 1, wherein R, the alkane, the alkene and the aromatic compound are unsubstituted.

8. The method of claim 1, wherein the organic compound comprises benzene.

9. The method of claim 1, wherein the at least one hydridohalosilane is trichlorosilane, dichlorosilane, methyldichlorosilane, or dimethylchlorosilane.

10. The method of claim 1, wherein the organohalosilane produced is phenyltrichlorosilane, diphenyldichlorosilane, phenylmethyldichlorosilane, or phenyldimethylchlorosilane.

11. The method of claim 1, wherein the hydridohalosilane is methyldichlorosilane and the organohalosilanes produced is phenylmethyldichlorosilane.

12. The method of claim 1, wherein the heterogeneous catalyst comprises γ-alumina.

13. The method of claim 1, wherein the pressure is from 4000 to 11000 kPa.

14. The method of claim 1, wherein the heterogeneous catalyst is treated with acid prior to the reacting of the organic compound and the hydridohalosilane.

15. A method for producing an organohalosilane, the method comprising:
1) treating a heterogeneous catalyst comprising an oxide of one or more of the elements Sc, Y, Ti, Zr, Hf, B, Al, Ga, In, C, Si, Ge, Sn, or Pb, with acid; and thereafter
2) reacting an organic compound comprising a halogen-substituted or unsubstituted alkane, a halogen-substituted or unsubstituted alkene, or an aromatic compound and at least one hydridohalosilane of $R_nSiH_mX_{4-m-n}$, wherein each R is independently $C_1$-$C_{14}$ hydrocarbyl or $C_1$-$C_{14}$ halogen-substituted hydrocarbyl, X is fluoro, chloro, bromo, or iodo, n is 0, 1, or 2, m is 1, 2 or 3, and m+n=1, 2 or 3, in the presence of the heterogeneous catalyst at a temperature greater than 100° C., and at a pressure of at least 690 kPa, to produce a crude reaction product comprising the organohalosilane.

16. A method for producing an organohalosilane, the method comprising:

reacting an organic compound comprising a halogen-substituted or unsubstituted alkane or an unsubstituted aromatic compound and at least one hydridohalosilane of formula $R_nSiH_mX_{4-m-n}$, wherein each R is independently $C_1$-$C_{14}$ hydrocarbyl or $C_1$-$C_{14}$ halogen-substituted hydrocarbyl, X is fluoro, chloro, bromo, or iodo, n is 0, 1, or 2, m is 1, 2 or 3, and m+n=1, 2 or 3, in the presence of a heterogeneous catalyst comprising an oxide of one or more of the elements Sc, Y, Ti, Zr, Hf, B, Al, Ga, In, C, Si, Ge, Sn, or Pb, at a temperature greater than 100° C., and at a pressure of at least 690 kPa, to produce a crude reaction product comprising the organohalosilane.

\* \* \* \* \*